United States Patent [19]

Sauer et al.

[11] Patent Number: 4,748,248

[45] Date of Patent: May 31, 1988

[54] PROCESS FOR THE PREPARATION OF ERGOLINE DERIVATIVES

[75] Inventors: Gerhard Sauer; Gregor Haffer, both of Berlin, Fed. Rep. of Germany

[73] Assignee: Schering Aktiengesellschaft, Berlin and Bergkamen, Fed. Rep. of Germany

[21] Appl. No.: 808,804

[22] Filed: Dec. 13, 1985

Related U.S. Application Data

[63] Continuation of Ser. No. 576,504, Feb. 2, 1984, abandoned, which is a continuation of Ser. No. 415,612, Sep. 3, 1982, abandoned.

[30] Foreign Application Priority Data

Sep. 3, 1981 [DE] Fed. Rep. of Germany ....... 3135305

[51] Int. Cl.$^4$ .......................................... C07D 457/12
[52] U.S. Cl. ....................................... 546/68; 546/67; 546/69
[58] Field of Search .................................... 548/68, 69

[56] References Cited

U.S. PATENT DOCUMENTS 4,379,790  4/1983  Horowski et al. .................... 546/68

FOREIGN PATENT DOCUMENTS 21206  1/1981  European Pat. Off. .

OTHER PUBLICATIONS

Baumgarten et al., "Reactions of Amines, XVIII, The Oxidative Rearrangement of Amides . . . ," J. Org. Chem. 40 (1975), pp. 3554–3561.

March, Jerry, *Advanced Organic Chemistry*, 2nd, McGraw-Hill, New York (1977), pp. 354–355.

Berde et al., *Ergot Alkaloids and Related Compounds*, Springer–Verlag, New York (1978), pp. 42–44, 53–56.

Baumgarten et al., "Reaction of Amines, XVIII, An Oxidative Rearrangement of Amids", *J.A.C.S.*, 87 (1965), pp. 1141–1142.

*Primary Examiner*—Donald G. Daus
*Assistant Examiner*—Cecilia Shen
*Attorney, Agent, or Firm*—Millen & White

[57] ABSTRACT

A process for preparing an ergoline of the formula

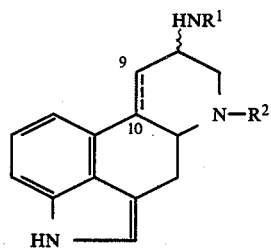

wherein
C$_9$----C$_{10}$ is a CC single or double bond,
R$^1$ is hydrogen or CONR$_2$, R being hydrogen, methyl, or ethyl, and wherein NR' is in the α- or β-position,
R$^2$ is lower alkyl of up to 3 carbon atoms, and the salts thereof, comprises treating the corresponding ergolinyl carboxylic acid amide with lead(IV) acetate in an aprotic polar solvent; reacting the intermediarily formed corresponding isocyanate with water or with a reactive amine of up to 4 carbon atoms, (e.g. a mono- or dialkylamine of up to 4-C atoms); and, optionally, treating the resultant product with an acid to form the corresponding salt.

13 Claims, No Drawings

PROCESS FOR THE PREPARATION OF ERGOLINE DERIVATIVES

This is a continuation of application Ser. No. 576,504, filed Feb. 2, 1984, now abandoned, which is a continuation of application Ser. No. 415,612, filed Sept. 3, 1982 and now abandoned.

BACKGROUND OF THE INVENTION

The present invention relates to a process for preparing ergolinyl derivatives.

All ergolines producible by this invention are either known biologically active compounds per se, e.g., as dopaminergic and adrenergic agonists or are intermediates for the production of such compounds using fully conventional methods, e.g., for production of other compounds producible by this invention.

From the hydrazides of lysergic acid and isolysergic acid, it is known to use the Curtius rearrangement to produce the corresponding amines and derivatives thereof (ureas, urethanes). However, this process has the disadvantage that the azide formed from the hydrazide is not stable in its configuration under the reaction conditions. The respective amine or amine derivative becomes contaminated by the other 8-position isomer (A. Hoffmann, Helv. 30: 44 [1947] and F. Troxler, Helv. 30: 163 [1947]).

SUMMARY OF THE INVENTION

Accordingly, it is an object of this invention to provide a process for preparing 8α- and 8β-aminoergolines and the derivatives thereof in a simple manner, with high purity and without isomerization at the C-8 position.

Upon further study of the specification and appended claims, further objects and advantages of this invention will become apparent to those skilled in the art.

These objects have been attained by providing a process for preparing an ergoline of the formula

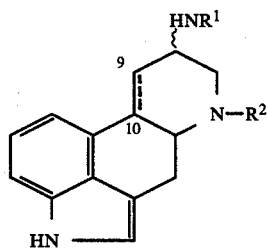

wherein $C_9 \text{-----} C_{10}$ is a CC single or double bond, $R^1$ is hydrogen or $CONR_2$, R being hydrogen, methyl, or ethyl, and wherein NR' is in the α- or β-position, $R^2$ is lower alkyl of up to 3 carbon atoms, and the salts thereof, comprising treating the corresponding ergolinyl carboxylic acid amide with lead (IV) acetate in an aprotic polar solvent; reacting the intermediarily formed corresponding isocyanate with water or with a reactive amine of up to 4 carbon atoms, (e.g. a mono- or dialkylamine of up to 4-C atoms);

and, optionally, treating the resultant product with an acid to form the corresponding salt.

DETAILED DISCUSSION

The process of this invention can be conducted, for example, by dissolving the 8α-ergoline carboxylic acid amide in an aprotic polar solvent and then gradually adding the lead (IV) acetate. In this process, the reaction temperature should not rise above room temperature. For this purpose, external cooling, for example with ice water, is suitably utilized. The reaction temperature usually is $-20°$ to $+20°$ C. Reaction times usually are 1-60 min.

Suitable solvents include, for example, reaction compatible, aprotic, polar solvents such as acetonitrile, hexamethylphosphoric triamide, dimethylformamide or dimethylacetamide, etc.

The lead (IV) acetate is usually used in an excess amount such as 1.5-4, preferably 1.75-2.5 molar equivalents, based on the starting acid amide. The amount of solvent usually is sufficient to achieve a complete dissolution of the corresponding ergoline carboxylic acid amide.

Subsequently, the reaction mixture which at this point contains 8α-ergoline isocyanate, is reacted with water in the presence of an acid, such as sulfuric or perchloric acid, to form the corresponding 8α-ergoline amine; or is reacted with a reactive amine, such as a mono- or dialkylamine, e.g. methylamine, dimethylamine, methylethylamine, or diethylamine, to form the corresponding 8α-ergolinyl urea derivative. This second stage is generally carried out at a temperature of 50°-100° C. for the hydrolysis reaction and 0°-50° C. for the reaction with the amine. Reaction times are usually 5-60 min. and 5-60 min., respectively. In the hydrolysis reaction, the amount of water usually is 10-1000 molar equivalents based on the number of molar equivalents of isocyanate in the original reaction mixture and the concentration of acid therein usually corresponds to a pH of 0-3. In the reaction with the amine, the amount of amine usually is 1-100 molar equivalents on the same basis.

Analogously, the 8β-ergoline carboxylic acid amide is reacted to form the ergoline 8β-amine or its urea derivatives.

The subsequent working-up step is performed in the usual way, such as by washing, filtration, recrystallization, extraction, and/or chromatography.

It has been found that the addition of an alkali or alkaline earth metal carbonate, such as sodium, potassium, or calcium carbonate, is advantageous during the lead acetate reaction. These compounds neutralize the acetic acid which is formed and, thus, prevent formation of acylamines by chemical addition of acetic acid from the lead (IV) acetate to the isocyanate. Such carbonates are used in amounts of 5-10 molar equivalents, based on the amount of ergoline employed. Since the first step is an essentially anhydrous reaction, anhydrous carbonates should be used.

If the desired final product is to be obtained in the form of an addition salt, the free compound, for example, can be dissolved in ethanol and reacted with the desired acid using fully conventional procedures. Suitable acids include all physiologically acceptable acids which produce physiologically acceptable salts, for example:

Hydrochloric acid, phosphoric acid, sulfuric acid, hydrobromic acid, nitrous acid or phosphorous acid; or organic acids, such as, for example, aliphatic mono- or di-carboxylic acids, phenyl-substituted alkanecarboxylic acids, hydroxyalkanecarboxylic acids, or alkanedicarboxylic acids, aromatic acids or aliphatic or aromatic sulfonic acids. Therefore, physiologically acceptable salts of these acids are, for example, the sulfate, bisulfate, phosphate, mono-hydrogen phosphate, dihydrogen phosphate, chloride, bromide, acetate, propionate, decanoate, caprylate, acrylate, formate, isobutyrate, caproate, heptanoate, propiolate, malonate, succinate, suberate, sebacate, hydrogen maleate, mandelate, butyne-1,4-dioate, hexyne-1,6-dioate, benzoate, chlorobenzoate, methylbenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycollate, tartrate, methanesulfonate, propanesulfonate, naphthalene-1-sulfonate, naphthalene-2-sulfonate, etc.

The course of the process of this invention is surprising since a skilled worker would have expected that the lead (IV) acetate would act on the indole portion of the ergoline molecule at C-3 or C-2, or on the alkaline nitrogen in the 6-position. See, for example various studies on indoles, such as, for example, in R. J. Sundberg, The Chemistry of Indoles in Organic Chemistry, Vol. 18, Academic Press, N.Y. and London, 1970, especially page 300, from which it would have to be expected that indole compounds would be attacked by lead (IV) acetate.

All starting material amides used in the process of this invention are known or readily preparable using fully conventional methods.

The yields of the process are high, usually 30–80 molar % with high configurational purities of final product of 98–100%.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

534.6 mg of isolysergic acid amide (2 millimoles) is dissolved in 10 ml of dimethylformamide. After adding 0.6 g of potassium carbonate, 1.8 g of lead (IV) acetate (98% strength, 4 mmol) is added in incremental portions under ice water cooling within 3 minutes; the reaction mixture is stirred for 5 minutes, and 8 ml of freshly distilled diethylamine is added dropwise thereto. After 10 minutes, the reaction solution, diluted with 50 ml of methylene chloride, is washed twice with respectively 10 ml of 16% aqueous ammonia solution and finally washed again with 500 ml of water. The organic phase, dried over magnesium sulfate and evaporated, is filtered over 50 g of aluminum oxide (neutral, activity stage II) with methylene chloride-ethyl acetate 80:20. The residue remaining after evaporation, consisting of 3-(9,10-didehydro-6-methyl-8α-ergolinyl)-1,1-diethylurea, is dissolved in 10 ml of ethanol; a solution of 0.25 g of maleic acid, dissolved in 5 ml of ethanol, is added, the mixture is evaporated to two-thirds its volume, and allowed to crystallize in a refrigerator overnight after adding seed crystals, thus isolating 0.51 g of 3-(9,10-didehydro-6-methyl-8α-ergolinyl)-1,1-diethylurea hydrogen maleate. $[\alpha]_D^{25} = +288°$; c=0.5 (methanol).

EXAMPLE 2

As described in Example 1, 267.3 mg of isolysergic acid amide (1 mmol) is reacted with lead (IV) acetate. The reaction mixture is then gently introduced into 25 ml of 1-normal sulfuric acid, previously heated to 85° C., stirred for 5 minutes at 80° C., mixed after cooling with 2 g of sodium bicarbonate in incremental portions, and further stirred for 15 minutes after adding 25 ml of methylene chloride. The entire reaction solution is filtered over kieselguhr, the aqueous phase is extracted twice with respectively 20 ml of methylene chloride, and the evaporation residue of the combined methylene chloride phases is filtered over silica gel with methanol-water 95:5, thus obtaining 84 mg of 9,10-didehydro-6-methylergoline-8α-amine. $[\alpha]_D^{25} = +260°$; c=0.5 (pyridine).

EXAMPLE 3

Analogously to Example 1, 295 mg of 9,10-didehydro-6-n-propyl-8α-ergoline carboxylic acid amide is reacted with lead (IV) acetate to the isocyanate, which latter compound reacts with diethylamine to the corresponding urea. After the reaction mixture has been worked up, chromatography on aluminum oxide with methylene chloride-ethyl acetate yields 120 mg of 3-(9,10-didehydro-6-n-propyl-8α-ergolinyl)-1,1-diethylurea.

Preparation of Starting Material

By allowing 3.1 g of the methyl ester of 9,10-didehydro-6-n-propyl-8β-ergoline carboxylic acid to stand in a solution of ammonia in ethylene glycol, a mixture of the isomeric amides is obtained; chromatographic separation of the reaction product yields 1.2 g of 9,10-didehydro-6-n-propyl-8α-ergoline carboxylic acid amide. $[\alpha]_D^{25} = +297°$; c=0.5 (pyridine).

EXAMPLE 4

538 mg of 6-methylergoline-8α-carboxylic acid amide (2 mmol) is reacted as described in Example 1 with lead (IV) acetate to the isocyanate. The latter is converted with diethylamine into 1,1-diethyl-3-(6-methyl-8α-ergolinyl)urea. Yield: 290 mg. $[\alpha]_D^{25} = +29°$; c=0.5 (chloroform).

Preparation of Starting Material

At −70° C., 100 mg of lithium is dissolved in approximately 10 ml of anhydrous ammonia and, at this temperature, 1 mmol of isolysergic acid amide and 1.5 mmol of aniline in 5 ml of tetrahydrofuran are added within a few minutes. If the solution shows discoloring, another small quantity of lithium is added. Then the mixture is stirred for 30 minutes at −70° C., combined with ammonium chloride until discoloring occurs, and the ammonia is removed by evaporation. The residue is taken up in saturated sodium bicarbonate solution, saturated with sodium chloride, and extracted with chloroform or ethyl acetate. The organic phase is dried with sodium sulfate, evaporated, and the residue is crystallized from ethanol, thus obtaining 6-methylergoline-8α-carboxylic acid amide in a 90% yield.

$[\alpha]_D^{25} = +2°$; c=0.5 (pyridine).

EXAMPLE 5

Analogously to Example 1, 6-n-propylergoline-8α-carboxylic acid amide, obtained by reducing 9,10-didehydro-6-n-propylergoline-8α-carboxylic acid amide with lithium in liquid ammonia, is reacted to 1,1-diethyl-3-(6-n-propyl-8α-ergolinyl)urea. After chromatography and reaction with tartaric acid, the compound is isolated as the tartrate. Yield: 45% of theory. $[\alpha]_D^{25} = +15°$; c=0.5 (pyridine).

EXAMPLE 6

Analogously to Example 1, 1 mmol of lysergic acid amide (267 mg) is oxidized with lead (IV) acetate, and the thus-formed isocyanate is reacted with diethylamine to 3-(9,10-didehydro-6-methyl-8β-ergolinyl)-1,1-diethylurea. Yield: 210 mg. $[\alpha]_D^{25} = +110°$; c=0.5 (pyridine).

EXAMPLE 7

As described in Example 2, 267 mg of lysergic acid amide (1 mmol) is reacted with lead (IV) acetate and worked up, thus obtaining 110 mg of 9,10-didehydro-6-methylergoline-8β-amine. $[\alpha]_D^{25} = +94°$; c=0.5 (pyridine).

The preceding examples can be repeated with similar success by substituting the generically or specifically described reactants and/or operating conditions of this invention for those used in the preceding examples. From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for preparing an ergoline of high configurational purity of the formula

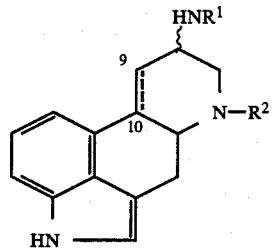

wherein
$NR^1$ can be in the α- or β-position,
$C_9 ---- C_{10}$ is a CC single or double bond,
$R^1$ is hydrogen or $CONR_2$,
R is hydrogen, methyl, or ethyl,
$R^2$ is lower alkyl of up to 3 carbon atoms, or a physiologically compatible salt thereof,
comprising,
treating the corresponding ergolinyl 8-carboxylic acid amide with lead (IV) acetate in a reaction compatible, aprotic polar solvent at a temperature less than about room temperature,
reacting the intermediarily formed corresponding 8-isocyanate with water or with a mono- or dialkylamine of up to 4 carbon atoms; and,
optionally, converting the resultant ergoline into a physiologically compatible salt thereof by reacting it with a corresponding acid.

2. A process of claim 1, further comprising adding an anhydrous alkali or alkaline earth metal carbonate to the reaction mixture during the lead (IV) acetate treatment step.

3. A process of claim 1 wherein the starting material ergolinyl compound and the resultant product have the 8α-configuration.

4. A process of claim 1 wherein the starting material ergolinyl compound and the resultant product have the 8β-configuration.

5. A process of claim 1 wherein the aprotic solvent is acetonitrile, hexamethylphosphoric triamide, dimethylformamide or dimethylacetamide.

6. A process of claim 1 wherein the isocyanate is reacted with water in the presence of an acid.

7. A process of claim 1 wherein the isocyanate is reacted with a mono- or dialkylamine.

8. A process of claim 1 wherein the amount of lead (IV) acetate is 1.5–4 molar equivalents based on the amount of starting acid amide used.

9. A process of claim 1, wherein $C_9 --- C_{10}$ is a double bond.

10. A process of claim 1, wherein the ergoline is produced selectively as the major product in high yield.

11. A process of claim 1, wherein the ergoline is produced in yields of about 30–80 molar %.

12. A process of claim 1, wherein the ergoline is produced with a configurational purity of 98%–100%.

13. A process of claim 1, wherein the ergoline is produced in yields of about 80 molar %.

* * * * *